United States Patent
Cox et al.

(10) Patent No.: US 10,376,679 B2
(45) Date of Patent: Aug. 13, 2019

(54) MEDICAL BALLOON WITH ENHANCED REFOLDING PROPERTIES

(71) Applicant: Biomerics FMI, LLC, Logan, UT (US)

(72) Inventors: Charles J. Cox, Eustace, TX (US); William F. Davies, Jr., Athens, TX (US); Lanny Pepper, Larue, TX (US)

(73) Assignee: Biomerics FMI, LLC, Athens, TX (US)

( * ) Notice: Subject to any disclaimer, the term of this patent is extended or adjusted under 35 U.S.C. 154(b) by 753 days.

(21) Appl. No.: 14/380,595

(22) PCT Filed: Mar. 6, 2013

(86) PCT No.: PCT/US2013/029460
§ 371 (c)(1),
(2) Date: Aug. 22, 2014

(87) PCT Pub. No.: WO2013/134437
PCT Pub. Date: Sep. 12, 2013

(65) Prior Publication Data
US 2015/0012032 A1    Jan. 8, 2015

Related U.S. Application Data

(60) Provisional application No. 61/607,576, filed on Mar. 6, 2012, provisional application No. 61/620,415, filed on Apr. 4, 2012.

(51) Int. Cl.
*A61M 25/10* (2013.01)

(52) U.S. Cl.
CPC .. *A61M 25/1002* (2013.01); *A61M 25/10184* (2013.11); *A61M 25/1038* (2013.01);
(Continued)

(58) Field of Classification Search
CPC ...... A61M 2025/1086; A61M 25/1002; A61M 25/1038; A61M 2025/1004;
(Continued)

(56) References Cited

U.S. PATENT DOCUMENTS 5,458,572 A * 10/1995 Campbell ........... A61M 25/104
604/103.08
5,478,319 A    12/1995 Campbell et al.
(Continued)

OTHER PUBLICATIONS

Patent Cooperation Treaty: International Search Report and Written Opinion for PCT/US2013/029460; Cox, Charles J.; dated May 20, 2013; 8 pages.

*Primary Examiner* — Katherine M Shi
(74) *Attorney, Agent, or Firm* — Med Venture Management, LLC; Daniel C. Higgs

(57) ABSTRACT

A medical balloon comprises a first end, a second end spaced apart from the first, and a generally cylindrical balloon wall extending therebetween to define an inflation chamber. The balloon wall is adapted for inflation from a first folded configuration having a first plurality of pleats to an expanded, unpleated configuration, and deflation therefrom to a second folded configuration having a second plurality of pleats. The balloon wall includes a first layer formed of a polymer and having a substantially constant radial thickness. A second layer is firmly attached to the first layer and has a plurality of first regions of greater radial thickness interleaved with a plurality of second regions of reduced radial thickness. During deflation from the expanded, unpleated configuration to the second folded configuration, the balloon wall folds along the regions of reduced radial thickness of the second layer to form the second plurality of pleats.

18 Claims, 14 Drawing Sheets

(52) U.S. Cl.
CPC ............... *A61M 25/10186* (2013.11); *A61M 2025/1004* (2013.01); *A61M 2025/1075* (2013.01); *A61M 2025/1084* (2013.01); *A61M 2025/1086* (2013.01)

(58) Field of Classification Search
CPC .. A61M 2025/1031; A61M 2025/1075; A61M 2025/1084; A61M 25/10; A61M 25/1027; A61M 25/1029; A61M 25/104; A61M 2025/1088; A61M 25/0043; A61M 25/1018; A61F 2/958
USPC ............ 606/191, 192, 194, 198; 604/103.06, 604/103.09, 96.01; 623/1.11
See application file for complete search history.

(56) References Cited

U.S. PATENT DOCUMENTS

| | | | |
|---|---|---|---|
| 6,010,480 A | 1/2000 | Abele et al. | |
| 6,884,234 B2* | 4/2005 | Aita | A61F 2/958 604/103.01 |
| 9,180,620 B2* | 11/2015 | Devens, Jr. | A61M 25/1002 |
| 2006/0015133 A1* | 1/2006 | Grayzel | A61F 2/958 606/192 |
| 2006/0276820 A1 | 12/2006 | Yamaguchi et al. | |
| 2007/0244501 A1* | 10/2007 | Horn | A61L 29/085 606/194 |
| 2008/0114294 A1 | 5/2008 | Holman et al. | |
| 2010/0042198 A1 | 2/2010 | Burton | |
| 2010/0243135 A1* | 9/2010 | Pepper | A61M 25/10 156/189 |
| 2011/0054513 A1 | 3/2011 | Pepper et al. | |
| 2011/0288478 A1 | 11/2011 | Ehrenreich et al. | |

\* cited by examiner

MEDICAL BALLOON WITH ENHANCED REFOLDING PROPERTIES

CROSS-REFERENCE TO RELATED APPLICATIONS

This application is a U.S. National Phase application submitted under 35 U.S.C. § 371of Patent Cooperation Treaty application serial no. PCT/US2013/029460, filed Mar. 6, 2013, published as international application WO 2013/134437, and entitled MEDICAL BALLOON WITH ENHANCED REFOLDING PROPERTIES. PCT/US2013/029460 claims benefit of and/or priority to U.S. Provisional Application 61/607,576, filed Mar. 6, 2012, entitled MEDICAL BALLOON WITH ENHANCED REFOLDING PROPERTIES and also claims benefit of and/or priority to U.S. Provisional Application 61/620,415, filed Apr. 4, 2012, entitled MEDICAL BALLOON WITH IMPROVED REFOLDING PROPERTIES. The specifications of PCT/US2013/029460, WO 2013/134437, U.S. application 61/607,576 and U.S. application 61/620,415 are incorporated herein by reference in their entirety.

TECHNICAL FIELD

The following disclosure relates to medical balloons. More particularly, it relates to medical balloons having a configuration that enhances the refolding properties of the balloon during deflation following inflation.

BACKGROUND

The use of medical balloons for treatment in the vascular system or other lumens of the body is well known. In a common situation, a medical balloon in a compact uninflated configuration mounted on a catheter shaft is inserted into the body via an introducer and guided through the vascular system. When the balloon reaches the desired treatment site within a body lumen, a fluid is injected through an inflation lumen in the catheter shaft to inflate the balloon. The balloon expands in an outward (i.e., radial) direction as it inflates, thereby dilating the body lumen at the treatment site. The fluid may then be withdrawn from the balloon via the inflation lumen, causing the balloon to deflate so that it can be moved to the next treatment site or withdrawn.

When the medical balloon is made from a noncompliant material, the uninflated balloon is typically folded into a pleated configuration and then the pleats are tightly wrapped circumferentially around the balloon to provide a low profile, thereby easing insertion of the uninflated balloon through the introducer and movement through the vascular system. Once the balloon is inflated, however, the pleats typically disappear, especially if the balloon is inflated to a high pressure. Upon deflation, the balloon may collapse in a random manner, forming a different number of pleats than originally present in the uninflated balloon. These randomly created pleats may have a larger, or otherwise less desirable, profile than that of the uninflated balloon. A need therefore exists, for a medical balloon with enhanced refolding properties during deflation.

SUMMARY OF THE INVENTION

In one aspect, a medical balloon comprises a first end member disposed at a distal end of a longitudinal axis, a second end member spaced apart from the first end member and disposed at a proximal end of the longitudinal axis, and a generally cylindrical balloon wall extending between the end members to define an inflation chamber. The balloon wall is adapted for inflation from a first folded configuration having a first plurality of pleats to an expanded, unpleated configuration and deflation from the expanded, unpleated configuration to a second folded configuration having a second plurality of pleats. The balloon wall includes a first layer and a second layer. The first layer is formed of a polymer and has, when viewed in cross section along the longitudinal axis, a substantially constant radial thickness around the circumference. The second layer is firmly attached to the first layer and has, when viewed in cross section along the longitudinal axis, a plurality of first regions of greater radial thickness interleaved with a plurality of second regions of reduced radial thickness. During deflation from the expanded, unpleated configuration to the second folded configuration, the balloon wall folds along the regions of reduced radial thickness of the second layer to form the second plurality of pleats.

In another aspect, a medical balloon comprises a first end member disposed at a distal end of a longitudinal axis, a second end member spaced apart from the first end member and disposed at a proximal end of the longitudinal axis, and a generally cylindrical balloon wall extending between the end members to define an inflation chamber which is adapted for inflation from a first folded configuration having a first plurality of pleats to an expanded, unpleated configuration and deflation from the expanded, unpleated configuration to a second folded configuration having a second plurality of pleats, the balloon wall including a first layer. The first layer is formed of a polymer and has, when viewed in cross section along the longitudinal axis, a substantially constant radial thickness around the circumference. A second layer is firmly attached to the first layer, the second layer having, when viewed in cross section along the longitudinal axis, a plurality of first regions of greater radial thickness interleaved with a plurality of second regions of reduced radial thickness. During deflation from the expanded, unpleated configuration to the second folded configuration, the balloon wall folds along the regions of reduced radial thickness of the second layer to form the second plurality of pleats.

In another embodiment, the first and second end members and the first layer of the balloon wall are integrally formed from a single piece of material and the second layer is formed from a different piece of material.

In still another embodiment, the first and second end members and the first layer of the balloon wall are formed from a single, seamless tube of material that has been blow-molded.

In yet another embodiment, the first and second end members and the first layer of the balloon wall are formed from a single, seamless tube of polyethylene terephthalate (PET) material.

In another embodiment, the first and second end members and the first layer of the balloon wall are formed from a single, seamless tube of nylon (polyamide) material.

In another embodiment, the second layer overlies, in the longitudinal direction, less than substantially the entire length of the balloon wall and does not overlie any of the first or second end members.

In another embodiment, the second layer overlies, in the longitudinal direction, substantially the entire length of the balloon wall but does not overlie any of the first or second end members.

In another embodiment, the second layer overlies, in the longitudinal direction, substantially the entire length of the balloon wall and at least a portion of the first and/or second end members.

In still another embodiment, the plurality of first regions of greater radial thickness interleaved with the plurality of second regions of reduced radial thickness extend, in the longitudinal direction, from at least a portion of the balloon wall onto at least a portion of one of the first and/or second end members.

In yet another embodiment, at least some of the second regions of reduced radial thickness include intermittent areas of different radial thickness along their longitudinal length.

In another embodiment, the second regions of reduced radial thickness are oriented substantially parallel to the longitudinal axis of the balloon.

In another embodiment, the second regions of reduced radial thickness are oriented substantially in the shape of a helix or spiral around the longitudinal axis of the balloon.

In another aspect, a medical balloon comprises a first end member disposed at a distal end of a longitudinal axis, a second end member spaced apart from the first end member and disposed at a proximal end of the longitudinal axis, and a generally cylindrical balloon wall extending between the end members to define an inflation chamber which is adapted for inflation from a first folded configuration having a first plurality of pleats to an expanded, unpleated configuration and deflation from the expanded, unpleated configuration to a second folded configuration having a second plurality of pleats, the balloon wall including a first layer. The first layer is formed of a polymer and has, when viewed in cross section along the longitudinal axis, a substantially constant radial thickness around the circumference. A second layer is firmly attached to the first layer, the second layer having, when viewed in cross section along the longitudinal axis, a plurality of first regions of greater radial thickness interleaved with a plurality of second regions of reduced radial thickness. The balloon further comprises at least one elongated reinforcing fiber member. During deflation from the expanded, unpleated configuration to the second folded configuration, the balloon wall folds along the regions of reduced radial thickness of the second layer to form the second plurality of pleats.

In another embodiment, the at least one elongated reinforcing fiber member comprises a plurality of elongated fiber members incorporated into the first layer and oriented substantially parallel to the longitudinal axis of the balloon.

In yet another embodiment, the at least one elongated reinforcing fiber member comprises a plurality of elongated fiber members incorporated into the second layer and oriented substantially parallel to the longitudinal axis of the balloon.

In still another embodiment, the plurality of elongated fiber members incorporated into the second layer are disposed within the first regions of greater radial thickness and not within the second regions of reduced radial thickness.

In another embodiment, the at least one elongated reinforcing fiber member is oriented substantially in the shape of a helix or spiral around the longitudinal axis of the balloon.

In another aspect, a medical balloon comprises a first end member disposed at a distal end of a longitudinal axis, second end member spaced apart from the first end member and disposed at a proximal end of the longitudinal axis, and a generally cylindrical balloon wall extending between the end members to define an inflation chamber which is adapted for inflation from a first folded configuration having a first plurality of pleats to an expanded, unpleated configuration and deflation from the expanded, unpleated configuration to a second folded configuration having a second plurality of pleats, the balloon wall including a first layer. The first layer is formed of a polymer and has, when viewed in cross section along the longitudinal axis, a substantially constant radial thickness around the circumference. A second layer is firmly attached to the first layer, the second layer having, when viewed in cross section along the longitudinal axis, a plurality of first regions of relatively greater longitudinal stiffness interleaved with a plurality of second regions of relatively reduced longitudinal stiffness. The balloon further comprises a plurality of elongated reinforcing fiber members. During deflation from the expanded, unpleated configuration to the second folded configuration, the balloon wall folds along the regions of reduced longitudinal stiffness of the second layer to form the second plurality of pleats.

In another embodiment, at least some of the elongated reinforcing fibers are incorporated into the second layer, and the elongated reinforcing fibers incorporated into the second layer are disposed only within the first regions and not within the second regions.

In yet another embodiment, at least some of the elongated reinforcing fibers are oriented substantially in the shape of a helix or spiral around the longitudinal axis of the balloon.

BRIEF DESCRIPTION OF THE DRAWINGS

For a more complete understanding, reference is now made to the following description taken in conjunction with the accompanying drawings in which.

DETAILED DESCRIPTION

Figure 1:
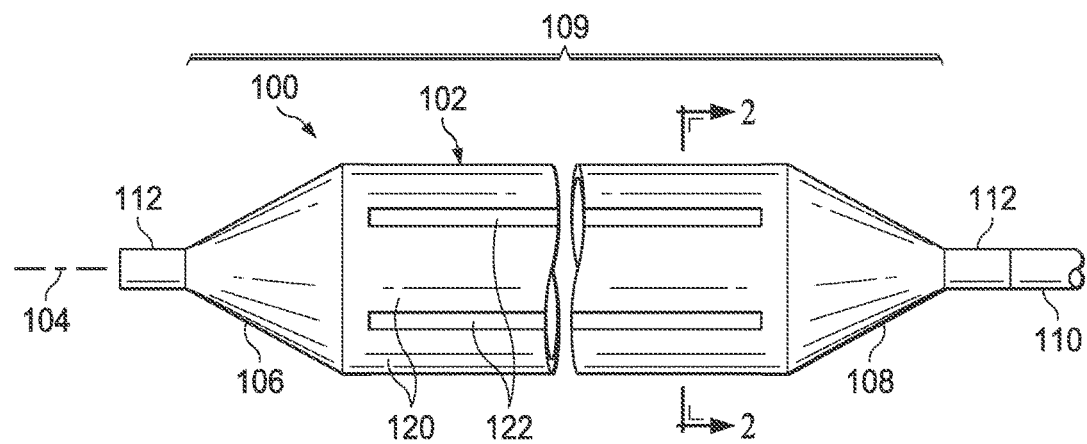
FIG. 1 is a side view of a medical balloon in accordance with one embodiment.

Referring to FIG. 1, there is illustrated a medical balloon according to one embodiment, shown in an inflated configuration. Medical balloon 100 includes a generally cylindrical balloon wall 102 that extends along a longitudinal axis 104 between a first end member 106 and a second end member 108. The first end member 106 may be located at the distal end of the balloon, e.g., the end farthest from the insertion point, and the second end member 108 may be located at the proximal end of the balloon, e.g., the end nearest to the insertion point. A catheter shaft 110 is typically attached to the proximal end member 108. The catheter shaft 110 may include a guidewire lumen (FIG. 2) and an inflation lumen (not shown) which are operatively connected to the balloon 100. The end members 106, 108 may be cone shaped or otherwise tapered, and may further include a neck 112 at one or both ends.

Figure 2:
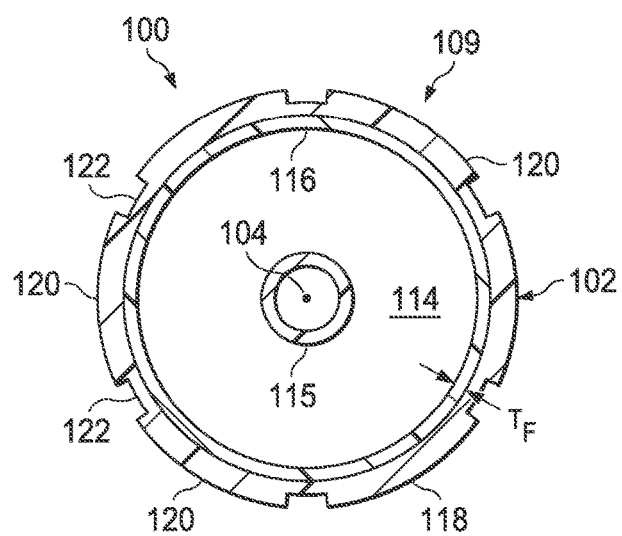
FIG. 2 is a cross-sectional view of the balloon of FIG. 1 taken along line 2-2 of FIG. 1.

Referring now also to FIG. 2, the balloon wall 102, together with the end members 106 and 108, form a pressure-tight exterior envelope 109 defining an inflation chamber 114 that is adapted to receive inflation fluid (i.e., via the inflation lumen of the catheter shaft). An inner shaft 115 enclosing the guidewire lumen may extend from the catheter shaft 110 through the inflation chamber 114 of the balloon 100. As best seen in FIG. 2, the exterior envelope 109 includes a first layer 116 and a second layer 118. The first layer 116 is formed of a polymer and, when viewed in cross section along the longitudinal axis 104, has a substantially constant radial thickness $T_F$ around the circumference. The second layer 118 is firmly attached to the first layer 116, and has, when viewed in cross section along the longitudinal axis 104, a plurality of first regions 120 of relatively greater radial thickness interleaved with a plurality of second regions 122 of relatively reduced radial thickness (i.e., compared to the first regions). The second layer 118 may extend over the entire exterior envelope 109, or it may be applied to only a portion of the exterior envelope. In the embodiment illustrated in FIG. 1, the second layer 118 extends over the entire area of the balloon wall 102; however, in other embodiments, the second layer may extend over only a part or parts of the balloon wall. In still other embodiments, the second layer 118 may extend over all or part of the end members (cones) 106 and 108, whether or not it also covers any of the balloon wall 102.

Although the second layer 118 forms, along with the first layer 116, portions of the pressure-tight envelope 109, the second layer is not necessarily pressure-tight itself. As will be further described, the second layer 118 may be configured with various slots, passages or the like such that fluids could pass therethrough were in not for the underlying first layer 116 to which the second layer is affixed.

In some embodiments, the first and second end members 106, 108 and the first layer 116 of the balloon wall 102 are integrally formed from a single piece of material and the second layer 118 is formed from a different piece of material. For example, the first and second end members 106, 108 and the first layer 116 of the balloon wall 102 may be formed from a single, seamless tube of material that has been blow-molded. In some embodiments, the first and second end members 106, 108 and the first layer 116 of the balloon wall 102 are formed from a single, seamless tube of polyethylene terephthalate (i.e., PET or PETE) material. In other embodiments, the first and second end members 106, 108 and the first layer 116 of the balloon wall 102 are formed from a single, seamless tube of nylon (i.e., polyamide) material.

Referring still to FIG. 2, it will be appreciated that, while the /radial thickness $T_F$ of the first layer 116 is substantially constant around the circumference for a particular cross section, the radial thickness of the first layer may vary along the longitudinal axis. For example, the radial thickness of the first layer 116 in the end member 106 (especially near the neck 112) may be greater than the radial thickness of the first layer in the balloon wall 102. In other words, cross sections taken at two different positions along the longitudinal axis 104 may have different values for the first layer radial thicknesses $T_F$; however, the thickness $T_F$ at each longitudinal location will be substantially constant around the circumference of the first layer.

Figure 3:
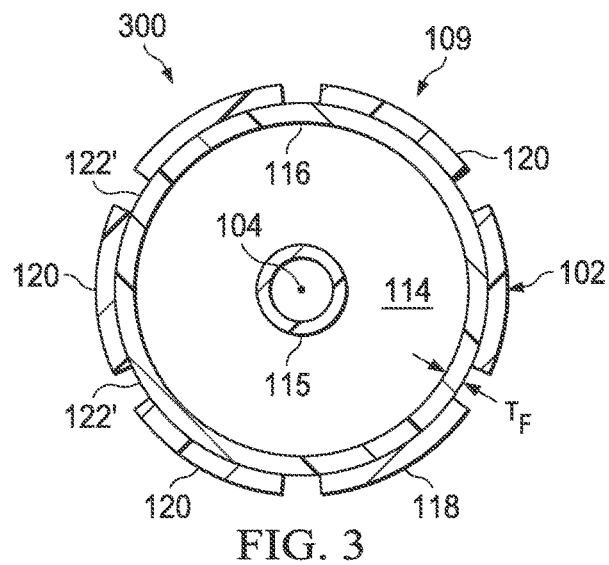
FIG. 3 is a cross-sectional view of a medical balloon in accordance with an alternative embodiment.

Referring now also to FIG. 3, it will be appreciated that, in some embodiments, the thickness of some or all of the second regions 122 may be zero, e.g., the second regions may be gaps (denoted 122') interleaved between the first regions 120. FIG. 3 illustrates a cross section of such an alternative embodiment. Balloon 300 is otherwise similar to the embodiment shown in FIGS. 1 and 2.

Figure 4:
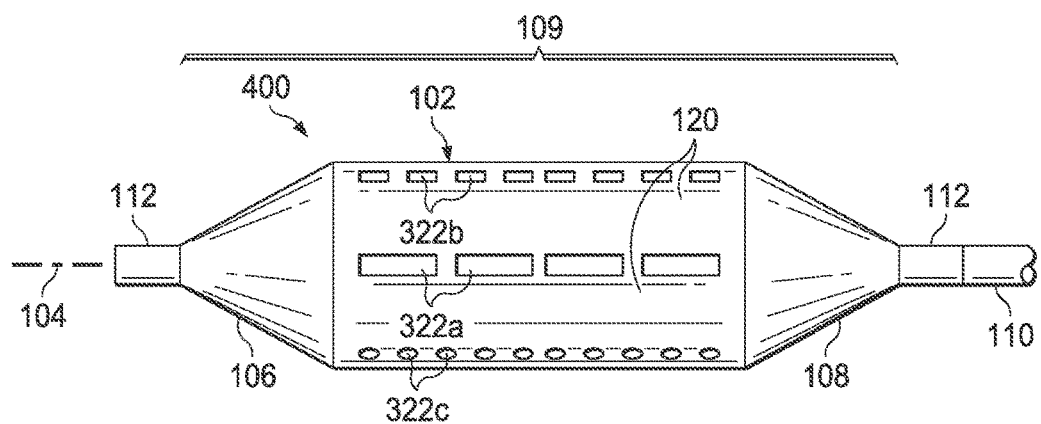
FIG. 4 is a side view of a medical balloon in accordance with yet another embodiment.

Referring now also to FIG. 4, in some embodiments, the first regions 120 and second regions 122 may extend along the balloon wall 102 continuously in the longitudinal direction for substantially the length of the balloon wall (as in FIG. 1). In other embodiments, the first regions 120 and/or the second regions 122 may comprise lines of discontinuous segments, "dashes," or "dots" extending along the balloon wall 102 in the longitudinal direction. FIG. 4 illustrates such an alternative embodiment including second regions of reduced thickness 322a configured as segments, second regions of reduced thickness 322b configured as "dashes" and second regions of reduced thickness 322c configured as "dots." Balloon 400 is otherwise similar to the embodiment shown in FIGS. 1 and 2. It will be appreciated that second regions of reduced thickness may be configured in other shapes in other embodiments.

Accordingly, in some embodiments, the second layer 118 may overlie, in the longitudinal direction, less than substantially the entire length of the balloon wall 102 and does not overlie any of the first or second end members 106 and 108. In other embodiment, the second layer 118 may overlie, in the longitudinal direction, substantially the entire length of the balloon wall 102 but does not overlie any of the first or second end members 106 and 108. In still other embodiment, the second layer 118 may overlie, in the longitudinal direction, substantially the entire length of the balloon wall 102 and at least a portion of the first and/or second end members 106 and 108.

Further, in some embodiments, the plurality of first regions 120 of greater radial thickness interleaved with the plurality of second regions 122 of reduced radial thickness may extend, in the longitudinal direction (i.e., along axis 104), from at least a portion of the balloon wall 102 onto at least a portion of one of the first and/or second end members 106 and 108. In other embodiments, at least some of the second regions 122 of reduced radial thickness may include intermittent areas (e.g., intermittent segments 322*a*, dashes 322*b* and/or dots 322*c* shown in FIG. 4) of different radial thickness along their longitudinal length. In some embodiments, the second regions 122 of reduced radial thickness may be oriented substantially parallel to the longitudinal axis 104 of the balloon (e.g., FIGS. 1, 4 and 8); whereas in other embodiments, the second regions 122 of reduced radial thickness are oriented substantially in the shape of a helix or spiral around the longitudinal axis of the balloon (e.g., FIGS. 7 and 9).

Figure 5A:
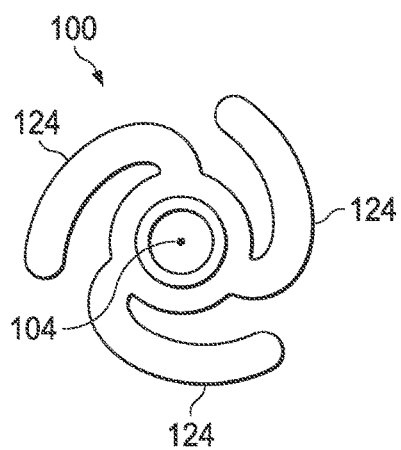
FIG. 5A is an end view of the balloon of FIG. 1 in the uninflated configuration.
Figure 5B:
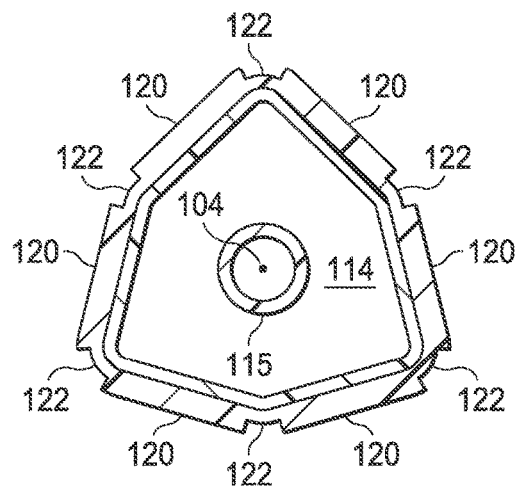
FIG. 5B is a cross-sectional end view of the balloon of FIG. 1 in the early stage of deflation after inflation.
Figure 5C:
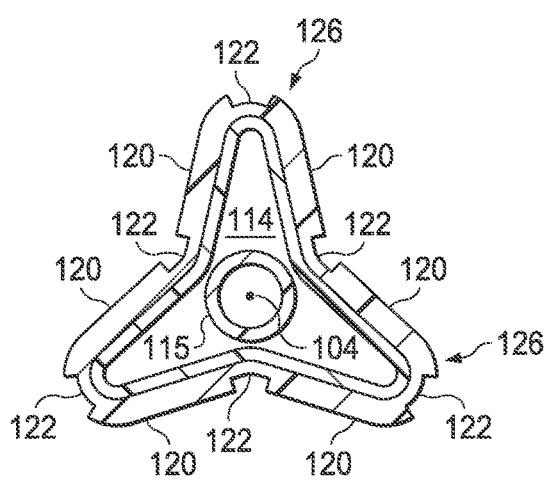
FIG. 5C is a cross-sectional end view of the balloon of FIG. 1 in a later stage of deflation following that shown in FIG. 5B.

Referring now also to FIGS. 5A, 5B and 5C, the balloon wall 102 is flexible enough that it may be folded into a first uninflated configuration, illustrated in FIG. 5A, having a plurality of flattened regions known as "pleats." In FIG. 5A, three original pleats are shown, but it will be appreciated that in other embodiments, the balloon may have 2, 4, 5, 6 or more original pleats. The original pleats 124 in the uninflated configuration may be wrapped circumferentially around the longitudinal axis 104 (and the inner shaft 115) to provide a low profile for the uninflated balloon 100. When inflation fluid enters the inflation chamber 114, the balloon 100 transforms from the uninflated configuration to an expanded, unpleated configuration (illustrated in FIG. 2). As the pressure within the inflation chamber 114 increases, the exterior envelope wall becomes more circular (i.e., when viewed in cross section along the longitudinal axis 104) and the original pleats 124 may no longer be present.

When the inflation fluid is subsequently withdrawn after inflation, the balloon 100 deflates from the expanded, unpleated configuration to a second folded configuration having a second plurality of pleats. FIG. 5B illustrates the balloon 100 in an early stage of deflation, and FIG. 5C shows a subsequent stage of deflation. The exterior envelope wall 109 folds along the regions 122 of reduced radial thickness of the second layer 118 to form the plurality of second pleats 126. In the embodiment shown, the number of second pleats 126 formed after deflation is the same as the number of original pleats 124 of the uninflated configuration, however, this is not required. In other words, the number of second pleats 126 may be more, less or equal to the number of original pleats 124.

In some embodiments, the first layer 116 of the exterior envelope 109 may be made from a single layer of polymer material, e.g., PETE, Pebax, nylon or other materials known for use in medical balloons. In other embodiments the first layer 116 may include multiple layers of polymer materials and/or reinforcing materials including fibers, woven fabrics, non-woven materials and or braided materials. Similarly, the second layer 118 may be made from a single layer of polymer material, e.g., PETE, Pebax, nylon or other materials known for use in medical balloons, or it may include multiple layers of polymer materials and/or reinforcing materials including fibers, woven fabrics, non-woven materials and or braided materials. In some embodiments, the second layer 118 may be attached to the first layer 116 using adhesive materials, in other embodiments the layers 118 and 116 may be attached using solvent welding, and in still other embodiments, the layers 118 and 116 may be attached using thermal welding.

Figure 6:
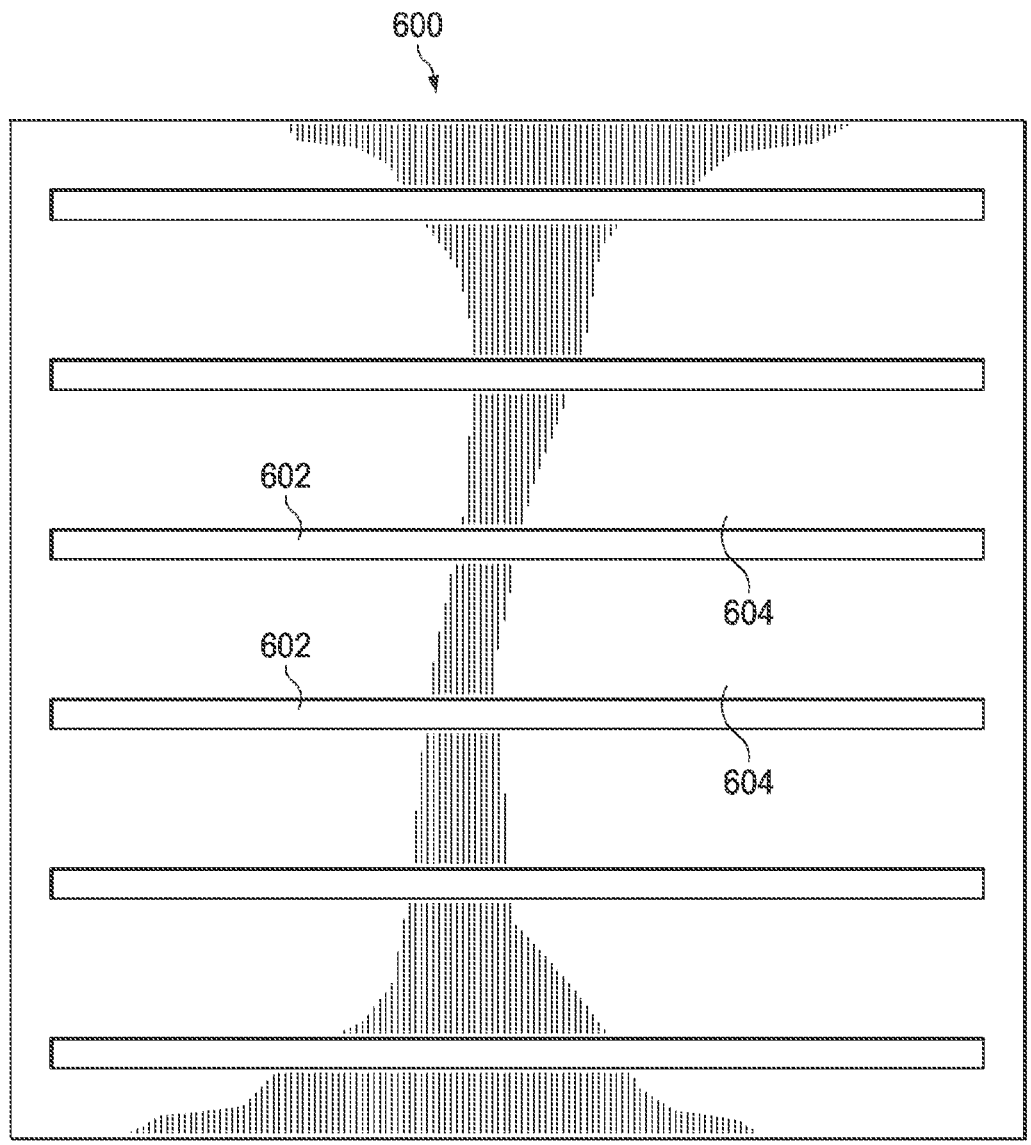
FIG. 6 is a side view of an appliqué that can be used to form the second layer of the medical balloon of FIG. 1.

Referring now to FIG. 6, there is illustrated an appliqué 600 that may be used to form the second layer 118. In this embodiment, the appliqué 600 includes a layer of polymer material having a plurality of cut-out slits 602. The appliqué 600 can then be attached over a conventionally formed balloon that serves as the first layer 116. The cut-out slits 602 of the appliqué 600 become the regions of reduced thickness 122 and the un-cut portions 604 become the regions of greater thickness 120.

Referring now to FIGS. 7, 8, 9, 10, 11B, 12B, 13B, 14B, 15B and 16B, there are illustrated additional medical balloons according to further embodiments. The medical balloons in these embodiments may include features substantially as described in connection with FIGS. 1-4, and like features are referred to using like reference numbers.

Figure 7:
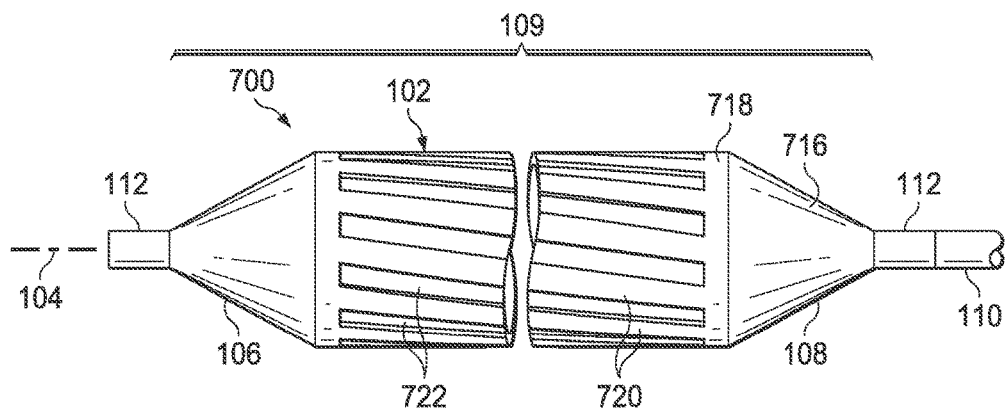
FIG. 7 is a side view of a medical balloon in accordance with an another alternative embodiment.

Referring now specifically to FIG. 7, there is illustrated a medical balloon 700 in accordance with another embodiment. The exterior envelope 109 of balloon 700 includes a first layer 716 and a second layer 718 that extends over the balloon wall 102. The second layer 718 includes a plurality of first regions 720 of relatively greater radial thickness interleaved with a plurality of second regions 722 of relatively reduced radial thickness. The second regions 722 in this embodiment are disposed in a "spiral" or "helical" configuration relative to the longitudinal axis 104. In the embodiment illustrated in FIG. 7, the second regions 722 are slots cut entirely through the second layer 718; however, in other embodiments the second regions may be thinned regions rather than slots.

Figure 8:
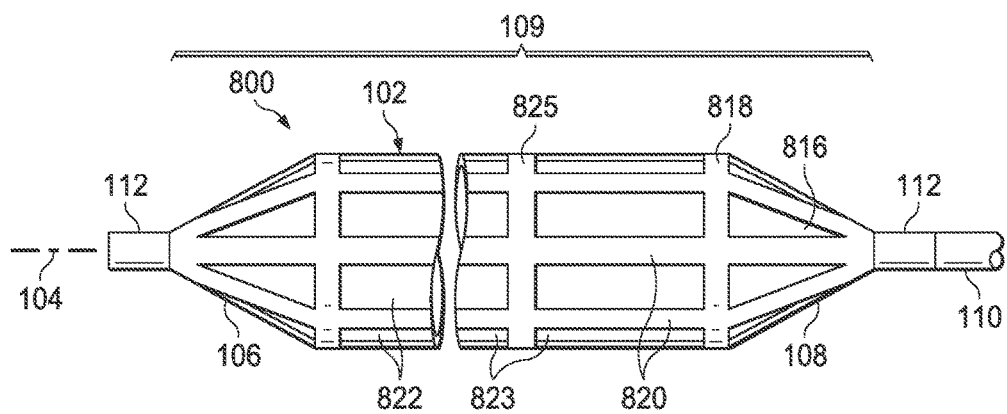
FIG. 8 is a side view of a medical balloon in accordance with an another alternative embodiment.

Referring now specifically to FIG. 8, there is illustrated a medical balloon 800 in accordance with another embodiment. The exterior envelope 109 of balloon 800 includes a first layer 816 (visible through the "cutouts" in the second layer) and a second layer 818 that extends over the balloon wall 102 and at least a portion of the end cones 106 and 108. The second layer 818 includes a plurality of first regions 820 of relatively greater radial thickness interleaved with a plurality of second regions 822 of relatively reduced radial thickness. The second regions 822 in this embodiment are disposed in longitudinal "segments" 823 separated by "ribs" 825 of first region 820. In the embodiment illustrated in FIG. 8, the second regions 822 are holes cut entirely through the second layer 818; however, in other embodiments the second regions may be thinned regions rather than holes.

Figure 9:
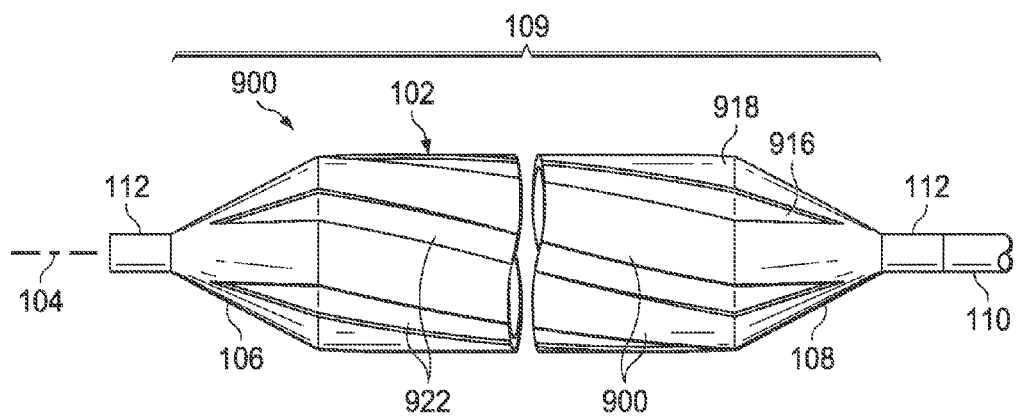
FIG. 9 is a side view of a medical balloon in accordance with an another alternative embodiment.

Referring now specifically to FIG. 9, there is illustrated a medical balloon 900 in accordance with another embodiment. The exterior envelope 109 of balloon 900 includes a first layer 916 (visible through the "cutouts" in the second layer) and a second layer 918 that extends over the balloon wall 102 and at least a portion of the end cones 106 and 108. The second layer 918 includes a plurality of first regions 920 of relatively greater radial thickness interleaved with a plurality of second regions 922 of relatively reduced radial thickness. The second regions 922 in this embodiment are disposed in a "spiral" or "helical" configuration relative to the longitudinal axis 104. In the embodiment illustrated in FIG. 9, the second regions 922 are slots cut entirely through the second layer 918; however, in other embodiments the second regions may be thinned regions rather than slots.

Figure 10:
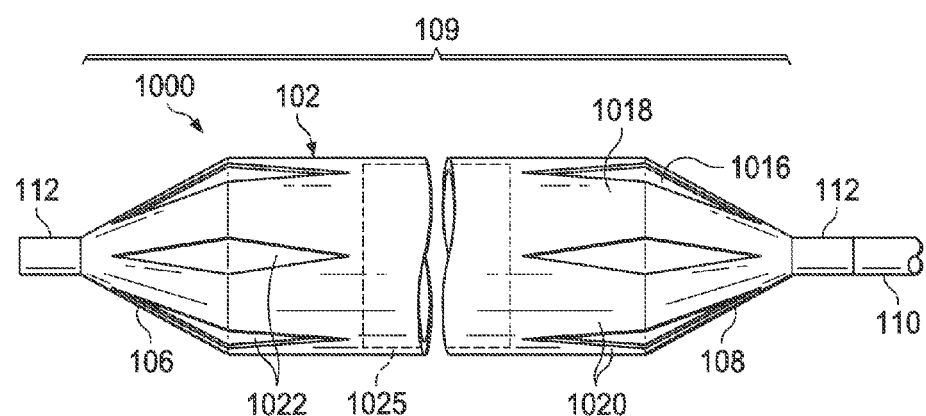
FIG. 10 is a side view of a medical balloon in accordance with an another alternative embodiment.

Referring now specifically to FIG. 10, there is illustrated a medical balloon 1000 in accordance with another embodiment. The exterior envelope 109 of balloon 1000 includes a first layer 1016 (visible through the "cutouts" in the second layer) and a second layer 1018 that extends over the balloon wall 102 and the end cones 106 and 108. The second layer 1018 includes a plurality of first regions 1020 of relatively greater radial thickness interleaved with a plurality of second regions 1022 of relatively reduced radial thickness. The second regions 1022 in this embodiment are configured as a plurality of "diamond"-shaped regions spanning the boundary between the balloon wall 102 and the end cones 106, 108. In the embodiment illustrated in FIG. 10, the second regions 1022 are holes cut entirely through the second layer 1018; however, in other embodiments the second regions may be thinned regions rather than holes. Also, in this embodiment the central portion 1025 (denoted by dotted lines) of the second layer 1018 is substantially uniform; however, in other embodiments, the central portion of the second layer may be omitted entirely, i.e., the second layer may not extend across the entire balloon wall.

Figure 11A:
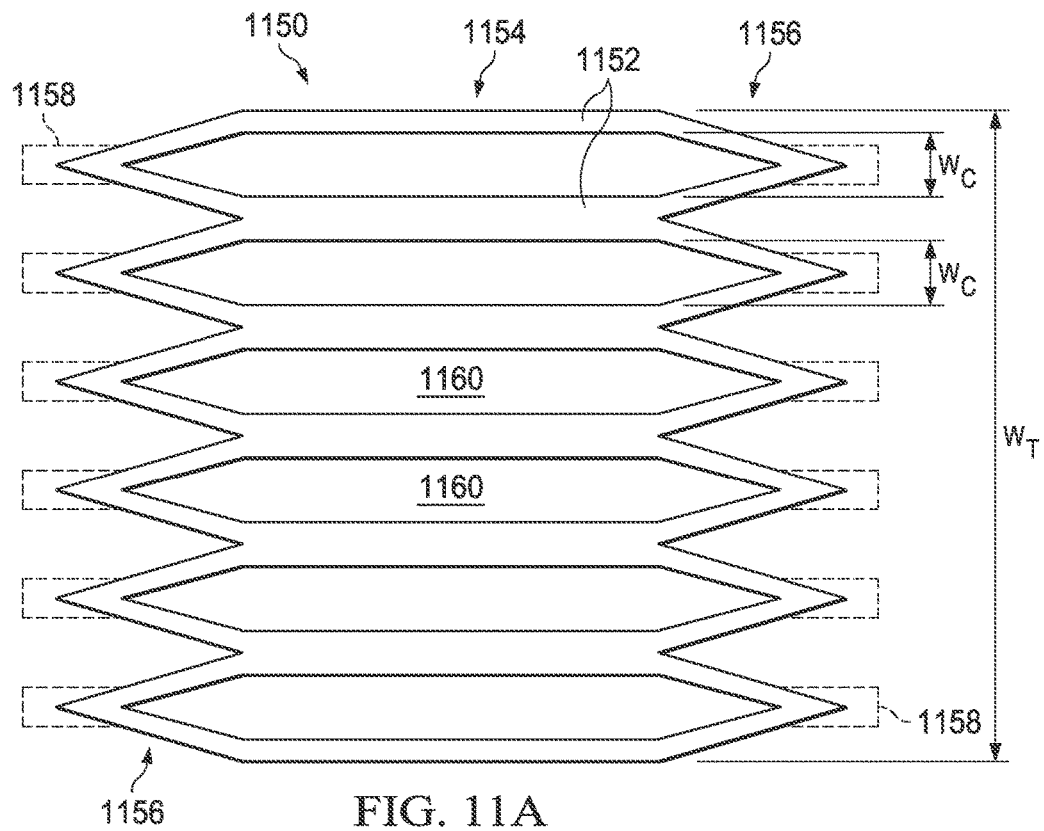
FIGS. 11A and 11B are, respectively, a side view of an appliqué that can be used to form the second layer of the medical balloon of FIG. 11B and a side view of a medical balloon in accordance with an another alternative embodiment.
Figure 11B:
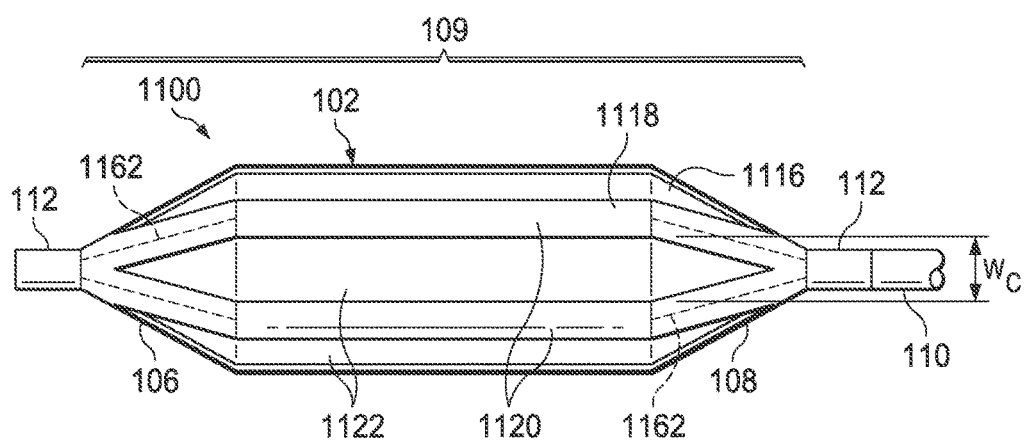

Referring now to FIGS. 11A and 11B, there is illustrated a medical balloon 1100 (FIG. 11B) in accordance with another embodiment, and an appliqué 1150 (FIG. 11A) that may be used as the second layer for the balloon. Referring first to FIG. 11B, the exterior envelope 109 of balloon 1100 includes a first layer 1116 (visible through the "cutouts" in the second layer) and a second layer 1118 that extends over the balloon wall 102 and the end cones 106 and 108. The second layer 1118 includes a plurality of first regions 1120 of relatively greater radial thickness interleaved with a plurality of second regions 1122 of relatively reduced radial thickness. The second regions 1122 in this embodiment run the entire length of the balloon wall 102 and span the boundary between the balloon wall 102 and the end cones 106, 108. Each of the second regions 1122 in this embodiment has the same circumferential width, denoted "$W_C$". In this embodiment, the second regions 1122 are circumferentially wide, i.e., the total circumferential width of the second regions (i.e., the sum of the $W_C$ for all of the second regions of the balloon) is greater than 50% of the overall balloon circumference, denoted $W_T$. In the embodiment illustrated in FIG. 11, the second regions 1122 are slots/holes cut entirely through the second layer 1118; however, in other embodiments the second regions may be thinned regions rather than holes.

Referring now to FIG. 11A, the appliqué 1150 includes a layer of polymer material 1152 including a central portion 1154 and a plurality of "pennants" 1156 disposed on opposing ends. The central portion 1154 is shaped to fit over the balloon wall 102 of the balloon 1100 and the pennants 1156 are shaped to (collectively) fit over the end cones 106, 108. In some embodiments, additional tabs 1158 (shown in dotted line) may extend from the pennants 1156 to facilitate attachment over the cones and/or neck portion of the balloon. To form the second regions 1122 of the balloon 1100, a plurality of triangular-ended slots 1160 having width $W_C$ are cut in the material 1152 (for an embodiment having thinned regions rather than holes, triangular-ended thinned regions may be substituted for the triangular-ended slots). The appliqué 1150 can then be wrapped around and attached over a conventionally formed balloon, such that the appliqué becomes the second layer 1118 and the original balloon becomes the first layer 1116. The cut-out triangular-ended slots 1160 of the appliqué 1150 become the regions of reduced thickness 1122 and the un-cut portions 1152 become the regions of greater thickness 1120. Note that in some embodiments, the material of the pennants 1156 and/or tabs 1158 may overlap in the cone or neck area (denoted in FIG. 11B by dotted lines 1162), thereby producing areas of greater thickness and or rigidity. While the appliqué 1150 just described may be used to form the second layer 1118 of the medical balloon 1100, it will be appreciated that the second layer may also be formed in other ways including, but not limited to attaching individual parts to the first layer 1116, pattern spraying, pattern printing and/or dipping.

Figure 12A:
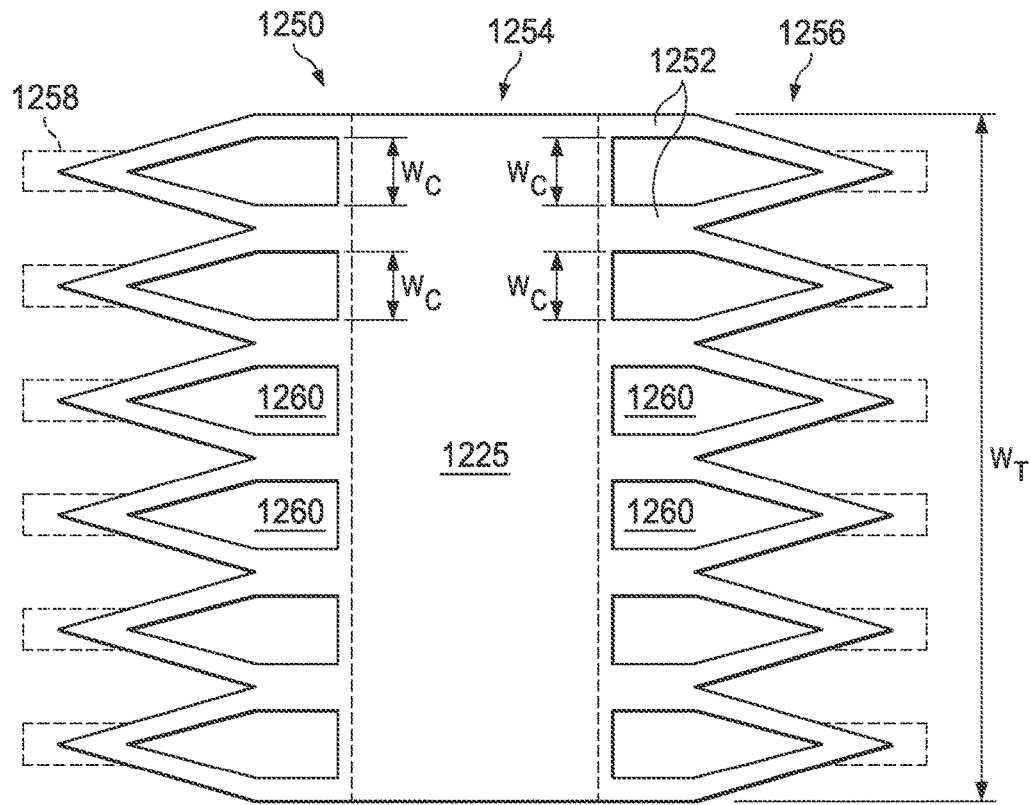
FIGS. 12A and 12B are, respectively, a side view of an appliqué that can be used to form the second layer of the medical balloon of FIG. 12B and a side view of a medical balloon in accordance with an another alternative embodiment.
Figure 12B:
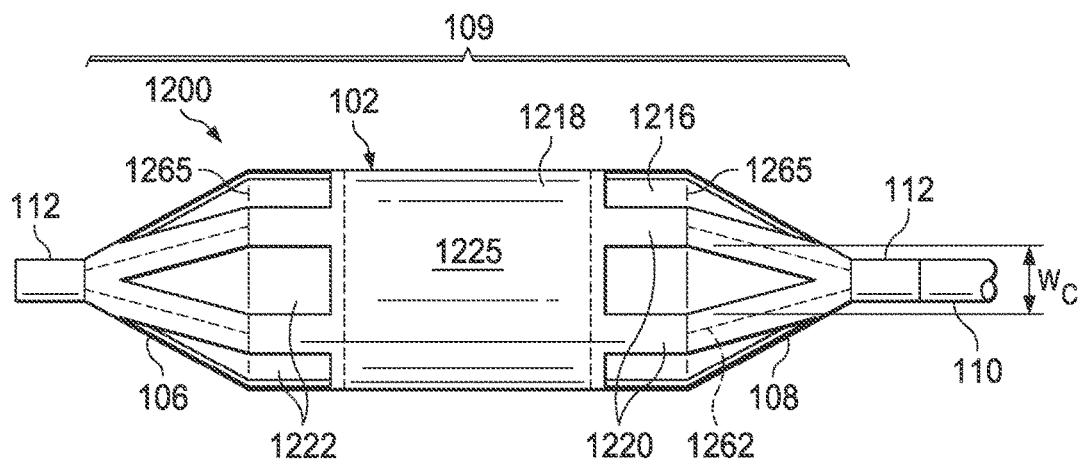

Referring now to FIGS. 12A and 12B, there is illustrated a medical balloon 1200 (FIG. 12B) in accordance with another embodiment, and an appliqué 1250 (FIG. 12A) that may be used as the second layer for the balloon. Medical balloon 1200 and appliqué 1250 are substantially similar to balloon 1100 and appliqué 1150 previously described, except that the second regions 1222 in this embodiment do not run the entire length of the balloon wall 102. Instead, the second regions 1222 span the boundaries 1265 between the balloon wall 102 and the end cones 106, 108, and extend a short distance in each longitudinal direction from the boundaries. In this embodiment, the second regions 1222 extend approximately equal distances from the boundaries 1265 onto the cones 106, 108 and the balloon wall 102. Each of the second regions 1222 in this embodiment has the same circumferential width $W_C$. Further, the total circumferential width of the second regions 1222 is greater than 50% of the overall balloon circumference $W_T$. Also, in this embodiment the central portion 1225 (denoted by dotted lines) of the second layer 1218 is substantially uniform; however, in other embodiments, the central portion of the second layer may be omitted entirely, i.e., the second layer be formed in two or more pieces that do not extend across the entire balloon wall.

Referring now to FIG. 12A, the appliqué 1250 includes a layer of polymer material 1252 including a central portion 1254 and a plurality of "pennants" 1256 disposed on opposing ends. The central portion 1254 is shaped to fit over the balloon wall 102 of the balloon 1200 and the pennants 1256 are shaped to (collectively) fit over the end cones 106, 108. In some embodiments, additional tabs 1258 may extend from the pennants 1256. To form the second regions 1222 of the balloon 1200, a plurality of triangular-ended slots 1260 having width $W_C$ are cut in the material 1252 (for an embodiment having thinned regions rather than holes, triangular-ended thinned regions may be substituted for the triangular-ended slots). In the embodiment shown, the "inner" ends of the slots 1260 are straight; however, in other embodiments, the slots may be triangular on both ends (as in FIG. 10). The appliqué 1250 can then be wrapped around and attached over a conventionally formed balloon, such that the appliqué becomes the second layer 1218 and the original balloon becomes the first layer 1216.

Figure 13A:
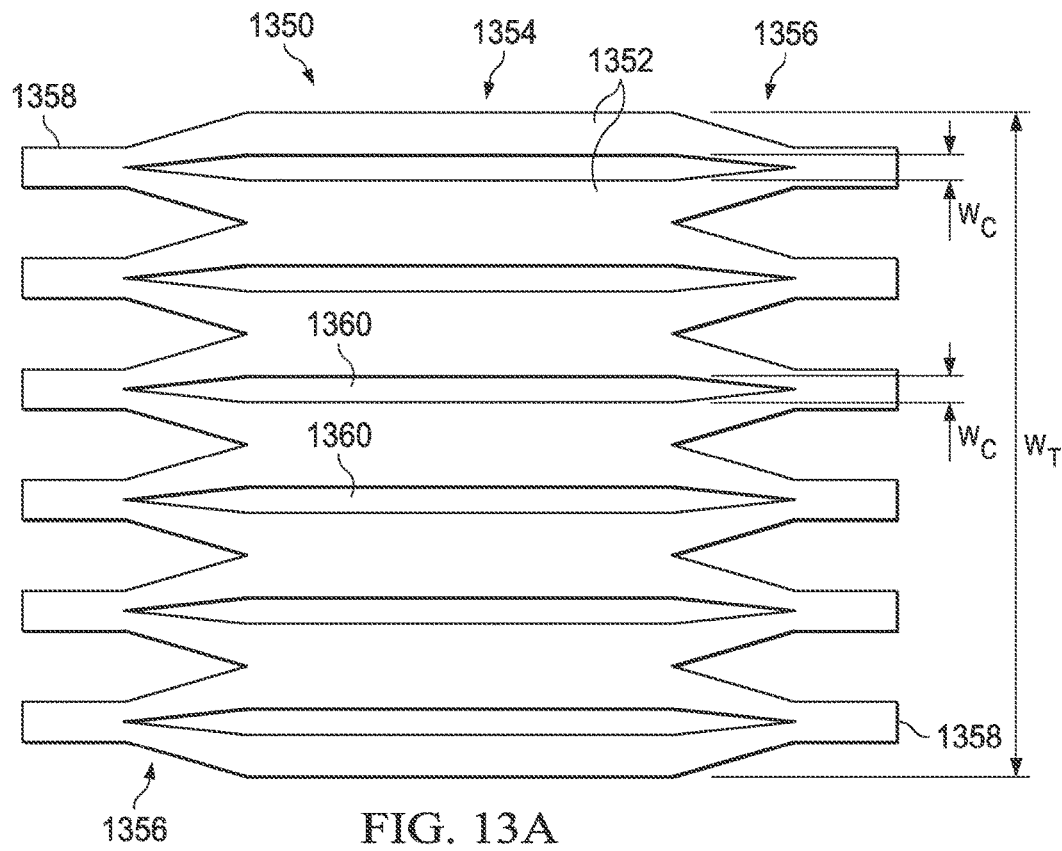
FIGS. 13A and 13B are, respectively, a side view of an appliqué that can be used to form the second layer of the medical balloon of FIG. 13B and a side view of a medical balloon in accordance with an another alternative embodiment.
Figure 13B:
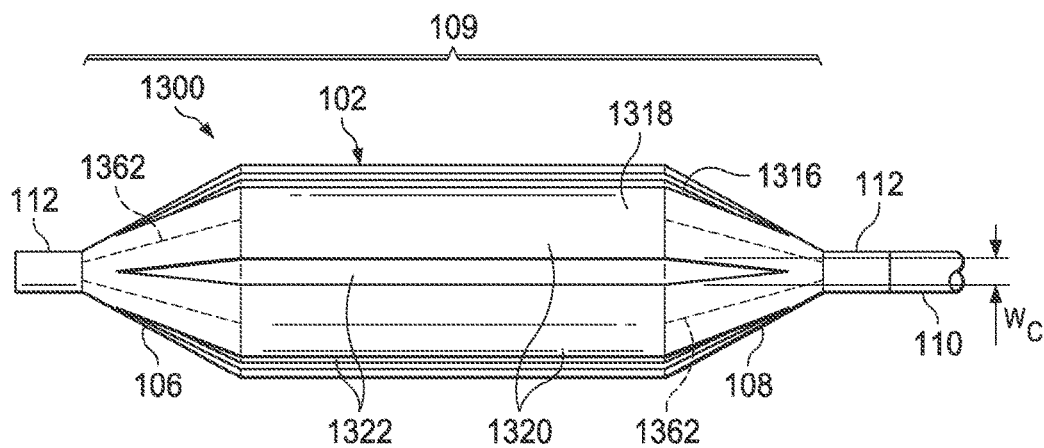

Referring now to FIGS. 13A and 13B, there is illustrated a medical balloon 1300 (FIG. 13B) in accordance with another embodiment, and an appliqué 1350 (FIG. 13A) that may be used as the second layer for the balloon. Referring first to FIG. 13B, the exterior envelope 109 of balloon 1300 includes a first layer 1316 (visible through the "cutouts" in the second layer) and a second layer 1318 that extends over the balloon wall 102 and the end cones 106 and 108. The second layer 1318 includes a plurality of first regions 1320 of relatively greater radial thickness interleaved with a plurality of second regions 1322 of relatively reduced radial thickness. The second regions 1322 in this embodiment run the entire length of the balloon wall 102 and span the boundary between the balloon wall 102 and the end cones 106, 108. Each of the second regions 1322 in this embodiment has the same circumferential width $W_C$. However, in this embodiment the second regions 1322 are circumferentially thin, i.e., the total circumferential width of the second regions 1322 is less than 50% of the overall balloon circumference $W_T$. In the embodiment illustrated in FIG. 13, the second regions 1322 are slots/holes cut entirely through the second layer 1318; however, in other embodiments the second regions may be thinned regions rather than holes.

Referring now to FIG. 13A, the appliqué 1350 includes a layer of polymer material 1352 including a central portion 1354, a plurality of pennant sections 1156 disposed on opposing ends and additional tabs 1358 extending from each pennant. To form the second regions 1322 of the balloon 1300, a plurality of triangular-ended slots 1360 having width $W_C$ are cut in the material 1352 (for an embodiment having thinned regions rather than holes, triangular-ended thinned regions may be substituted for the triangular-ended slots). The appliqué 1350 can then be wrapped around and attached over a conventionally formed balloon, such that the appliqué becomes the second layer 1318 and the original balloon becomes the first layer 1316. The cut-out triangular-ended slots 1360 of the appliqué 1350 become the regions of reduced thickness 1322 and the un-cut portions 1352 become the regions of greater thickness 1320. Note that in some embodiments, the material of the pennants 1356 and/or tabs 1358 may overlap in the cone or neck area (denoted in FIG. 13B by dotted lines 1362), thereby producing areas of greater thickness and or rigidity. While the appliqué 1350 just described may be used to form the second layer 1318 of the medical balloon 1300, it will be appreciated that the second layer may also be formed in other ways as described herein.

Figure 14A:
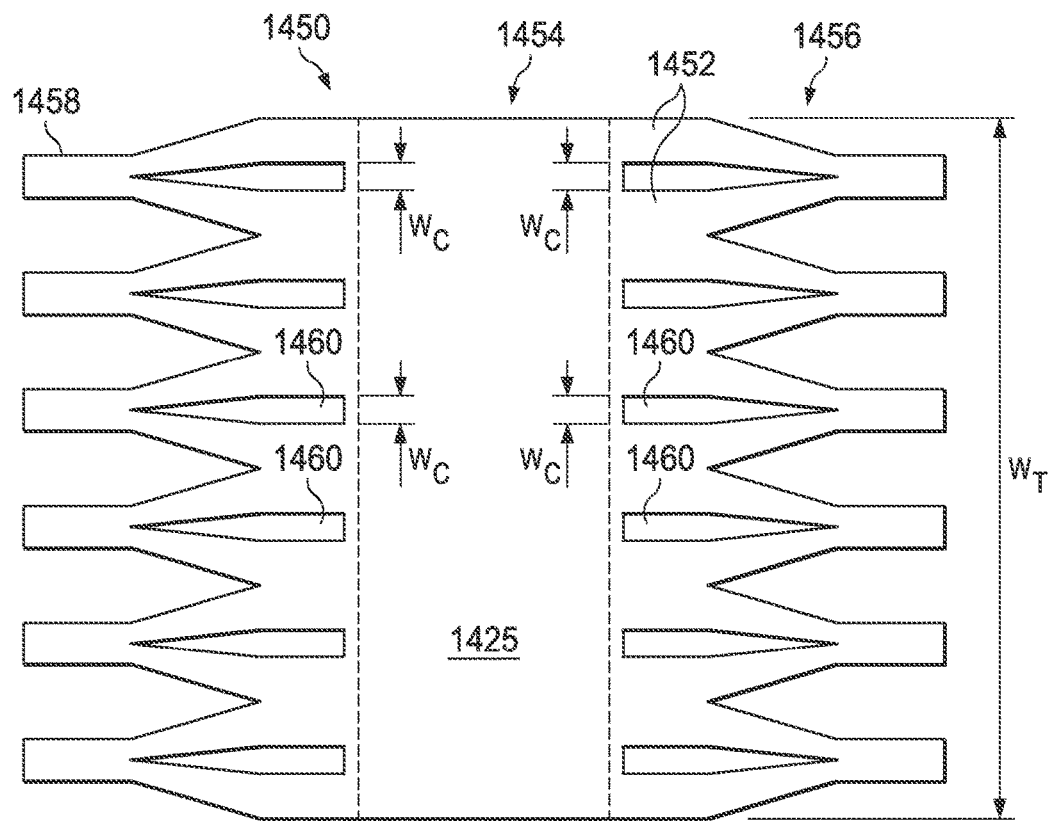
FIGS. 14A and 14B are, respectively, a side view of an appliqué that can be used to form the second layer of the medical balloon of FIG. 14B and a side view of a medical balloon in accordance with an another alternative embodiment.
Figure 14B:
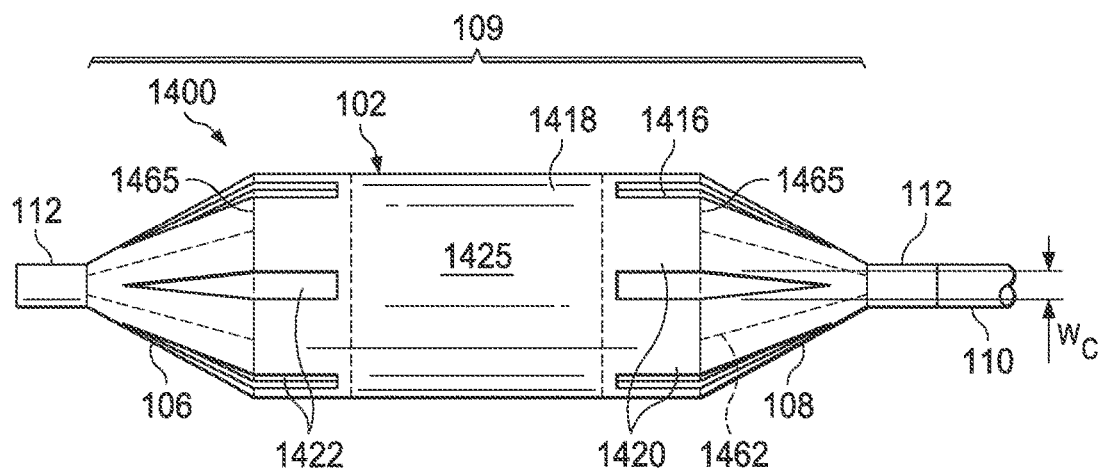

Referring now to FIGS. 14A and 14B, there is illustrated a medical balloon 1400 (FIG. 14B) in accordance with another embodiment, and an appliqué 1450 (FIG. 14A) that may be used as the second layer for the balloon. Medical balloon 1400 and appliqué 1450 are substantially similar to balloon 1300 and appliqué 1350 previously described, except that the second regions 1422 in this embodiment do not run the entire length of the balloon wall 102. Instead, the second regions 1422 span the boundaries 1465 between the balloon wall 102 and the end cones 106, 108, and extend a short distance in each longitudinal direction from the boundaries. In this embodiment, the second regions 1422 extend approximately equal distances from the boundaries 1465 onto the cones 106, 108 and the balloon wall 102. Each of the second regions 1422 in this embodiment has the same circumferential width $W_C$. The total circumferential width of the second regions 1422 is less than 50% of the overall balloon circumference $W_T$. Also, in this embodiment the central portion 1425 (denoted by dotted lines) of the second layer 1418 is substantially uniform; however, in other embodiments, the central portion of the second layer may be omitted entirely, i.e., the second layer be formed in two or more pieces that do not extend across the entire balloon wall.

Referring now to FIG. 14A, the appliqué 1450 includes a layer of polymer material 1452 including a central portion 1454, a plurality of pennants sections 1456 and additional tabs 1458 extending from the pennant section. To form the second regions 1422 of the balloon 1400, a plurality of triangular-ended slots 1460 having width $W_C$ are cut in the material 1452 (for an embodiment having thinned regions rather than holes, triangular-ended thinned regions may be substituted for the triangular-ended slots). In the embodiment shown, the "inner" ends of the slots 1460 are straight; however, in other embodiments, the slots may be triangular on both ends (as in FIG. 10). The appliqué 1450 can then be wrapped around and attached over a conventionally formed balloon, such that the appliqué becomes the second layer 1418 and the original balloon becomes the first layer 1416.

Figure 15A:
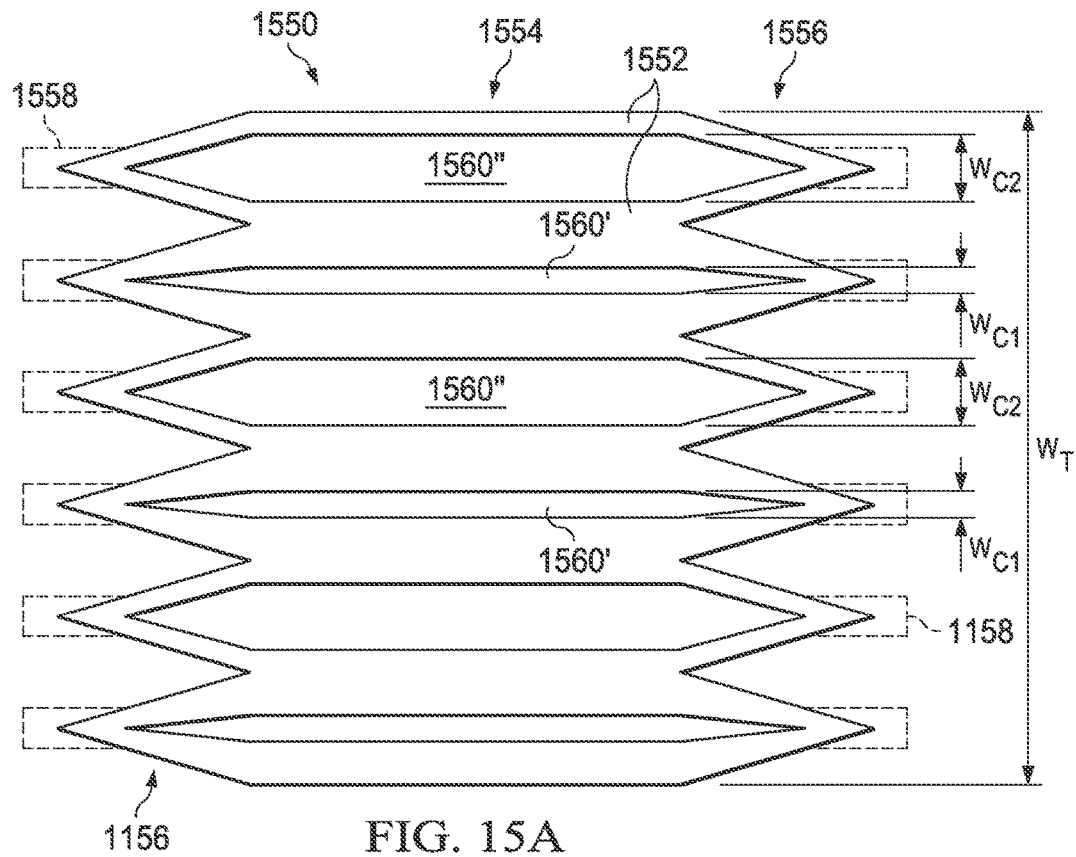
FIGS. 15A and 15B are, respectively, a side view of an appliqué that can be used to form the second layer of the medical balloon of FIG. 15B and a side view of a medical balloon in accordance with an another alternative embodiment.
Figure 15B:
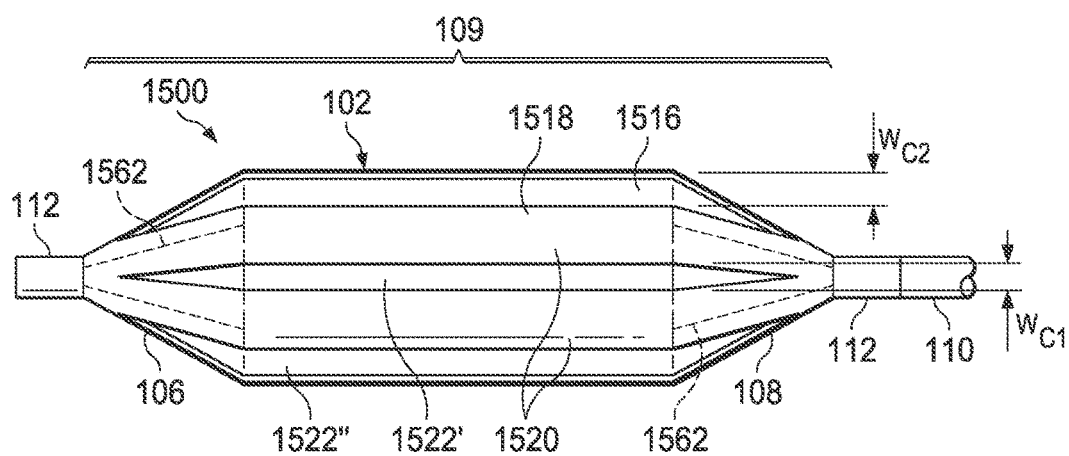

Referring now to FIGS. 15A and 15B, there is illustrated a medical balloon 1500 (FIG. 15B) in accordance with another embodiment, and an appliqué 1550 (FIG. 15A) that may be used as the second layer for the balloon. Referring first to FIG. 15B, the exterior envelope 109 of balloon 1500 includes a first layer 1516 (visible through the "cutouts" in the second layer) and a second layer 1518 that extends over the balloon wall 102 and the end cones 106 and 108. The second layer 1518 includes a plurality of first regions 1520 of relatively greater radial thickness interleaved with a plurality of second regions 1522 of relatively reduced radial thickness. The second regions 1522 in this embodiment run the entire length of the balloon wall 102 and span the boundary between the balloon wall 102 and the end cones 106, 108. Unlike the embodiments of FIGS. 11B, 12B, 13B and 14B, the second regions 1522 in this embodiment do not have the same circumferential width $W_C$. Instead, the second regions 1522 include first type second regions 1522' having a first form characteristic and second type second regions 1522" having a different form characteristic.

In this embodiment, the form characteristics of the second regions 1522 (i.e., first type 1522' and second type 1522") are the circumferential widths: the first type second regions 1522' have a first circumferential width, denoted $W_{C1}$, and the second type second regions 1522" have a second circumferential width, denoted $W_{C2}$. In other embodiments, the form characteristics may include other modifications to the second layer including, but not limited to, differences in region width, differences in region thickness (i.e., different degrees of thinning) and/or differences in region thinning direction (i.e., thinned from above or below). In the embodiment illustrated in FIG. 15, the second regions 1522 (of both types) are slots/holes cut entirely through the second layer 1518; however, in other embodiments the second regions may be thinned regions rather than holes, or the second regions of one type may be thinned while the second regions of the other type may be holes.

Further, in the embodiment illustrated in FIGS. 15A and 15B, the second regions 1522 with different form characteristics are disposed in a predetermined pattern around the circumference of the balloon 1500. In this embodiment, the first type second regions 1522' having circumferential width $W_{C1}$ alternate with the second type second regions 1522" having circumferential width $W_{C2}$. In other embodiments, other patterns for disposition around the balloon may be used.

Referring now to FIG. 15A, the appliqué 1550 includes a layer of polymer material 1552 including a central portion 1554, a plurality of pennants 1556 disposed on opposing ends and (optional) additional tabs 1558 (shown in dotted line) that may extend from each pennant. To form the second regions 1522 of the balloon 1500, a first plurality of triangular-ended slots 1560' having width $W_{C1}$ and a second plurality of triangular-ended slots 1560" having width $W_{C2}$ are cut in the material 1552 in an alternating pattern (for an embodiment having thinned regions rather than holes, triangular-ended thinned regions may be substituted for the triangular-ended slots). The appliqué 1550 can then be wrapped around and attached over a conventionally formed balloon, such that the appliqué becomes the second layer 1518 and the original balloon becomes the first layer 1516. The cut-out triangular-ended slots 1560' and 1560" of the appliqué 1550 become the regions of reduced thickness first type 1522' and second type 1522", respectively, and the un-cut portions 1552 become the regions of greater thickness 1520. Note that in some embodiments, the material of the pennants 1556 and/or tabs 1558 may overlap in the cone or neck area (denoted in FIG. 15B by dotted lines 1562), thereby producing areas of greater thickness and or rigidity. While the appliqué 1550 just described may be used to form the second layer 1518 of the medical balloon 1500, it will be appreciated that the second layer may also be formed in other ways as described herein.

Figure 16A:
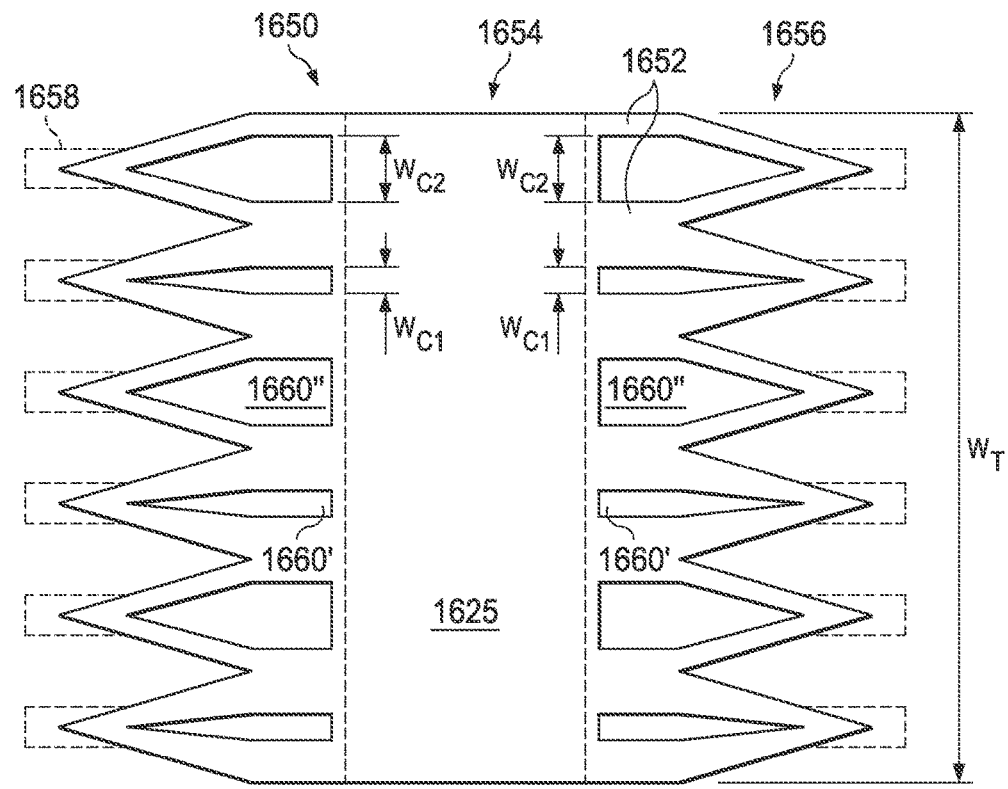
FIGS. 16A and 16B are, respectively, a side view of an appliqué that can be used to form the second layer of the medical balloon of FIG. 16B and a side view of a medical balloon in accordance with an another alternative embodiment.
Figure 16B:
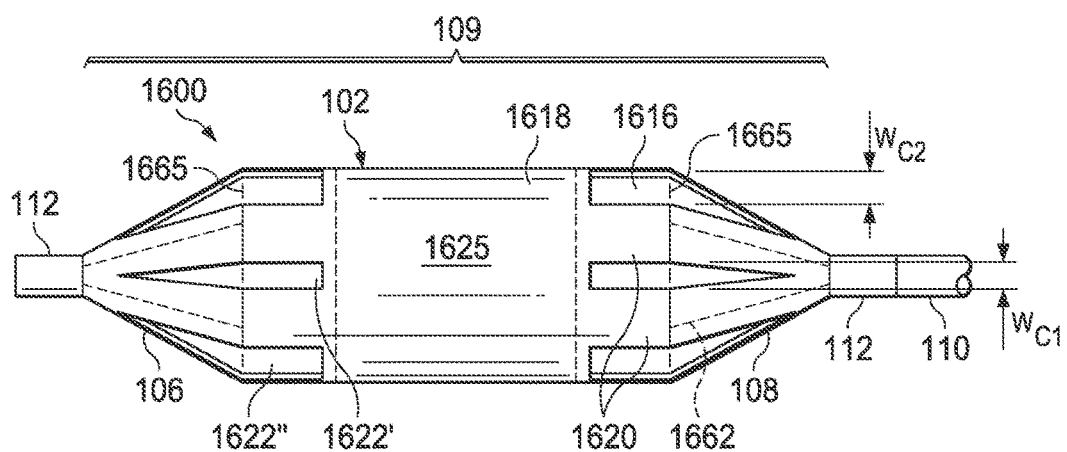

Referring now to FIGS. 16A and 16B, there is illustrated a medical balloon 1600 (FIG. 16B) in accordance with another embodiment, and an appliqué 1650 (FIG. 16A) that may be used as the second layer for the balloon. Medical balloon 1600 and appliqué 1650 are substantially similar to balloon 1500 and appliqué 1550 previously described, except that the second regions 1622 (both types 1622' and 1622") in this embodiment do not run the entire length of the balloon wall 102. Instead, the second regions 1622 span the boundaries 1665 between the balloon wall 102 and the end cones 106, 108, and extend a short distance in each longitudinal direction from the boundaries. In this embodiment, the second regions 1622 extend approximately equal distances from the boundaries 1665 onto the cones 106, 108 and the balloon wall 102. The first type second regions 1622' have a first circumferential width, denoted $W_{C1}$, and the second type second regions 1622" have a second circumferential width, denoted $W_{C2}$. Also, in this embodiment the central portion 1625 (denoted by dotted lines) of the second layer 1618 is substantially uniform; however, in other embodiments, the central portion of the second layer may be omitted entirely, i.e., the second layer be formed in two or more pieces that do not extend across the entire balloon wall.

Referring now to FIG. 16A, the appliqué 1650 includes a layer of polymer material 1652 including a central portion 1654, a plurality of pennants 1656 and (optional) additional tabs 1658 extending from the pennants. To form the second regions 1622 (i.e., 1622' and 1622") of the balloon 1600, a first plurality of triangular-ended slots 1660' having width $W_{C1}$ and a second plurality of triangular-ended slots 1660" having width $W_{C2}$ are cut in the material 1652 in an alternating pattern (for an embodiment having thinned regions rather than holes, triangular-ended thinned regions may be substituted for the triangular-ended slots). In the embodiment shown, the "inner" ends of the slots 1660 are straight; however, in other embodiments, the slots may be triangular on both ends (as in FIG. 10). The appliqué 1650 can then be wrapped around and attached over a conventionally formed balloon, such that the appliqué becomes the second layer 1618 and the original balloon becomes the first layer 1616.

Figure 17:
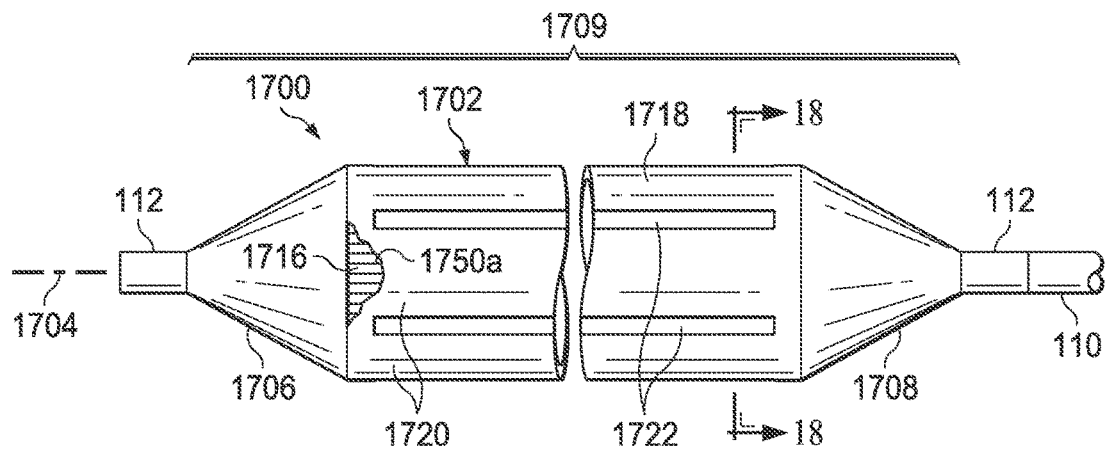
FIG. 17 is a side view, with portions broken away, of a medical balloon in accordance with another aspect of the invention.

Referring now to FIG. 17, there is illustrated a medical balloon in accordance with another embodiment of the invention. Medical balloon 1700 is substantially identical in many respects to the previously disclosed balloons, comprising a first end member 1706 disposed at a distal end of a longitudinal axis 104, a second end member 1708 spaced apart from the first end member and disposed at a proximal end of the longitudinal axis, and a generally cylindrical balloon wall 1702 extending between the end members to define an inflation chamber 1714. The balloon is adapted for inflation from a first folded configuration having a first plurality of pleats to an expanded, unpleated configuration and deflation from the expanded, unpleated configuration to a second folded configuration having a second plurality of pleats (similar to that illustrated in FIGS. 5a, 5b and 5c). The balloon wall 1702 includes a first layer 1716 formed of a polymer and having, when viewed in cross section along the longitudinal axis 104, a substantially constant radial thickness $T_F$ around the circumference. A second layer 1718 is firmly attached to the first layer 1716, the second layer having, when viewed in cross section along the longitudinal axis 104, a plurality of first regions 1720 of greater radial thickness interleaved with a plurality of second regions 1722 of reduced radial thickness. The balloon 1700 further comprises at least one (and typically many) elongated reinforcing fiber members 1750, which are incorporated into the pressure-tight envelope 1709 of the balloon, i.e., in the balloon wall 1702, end members 1706 and 1708, first layer 1716 and/or second layer 1718. During deflation from the expanded, unpleated configuration to the second folded configuration, the balloon wall 1702 folds along the regions 1722 of reduced radial thickness of the second layer 1718 to form the second plurality of pleats.

In some embodiments, the elongated reinforcing fiber members 1750 may include longitudinal reinforcing fibers 1750a. Such longitudinal reinforcing fibers 1750a may be substantially inelastic fibers which may be oriented parallel or substantially parallel to one another and may be parallel within ±10 degrees to the balloon's longitudinal axis 104. In other embodiments, the elongated reinforcing fiber members 1750 include so-called "hoop" reinforcing fibers 1750b. Such hoop reinforcing fibers 1750b may be substantially inelastic fibers and may be circumferentially- or hoop-oriented, parallel or substantially parallel to one another, and may be perpendicular within ±10 degrees to the longitudinal axis 104. In some embodiments, the reinforcing fiber member 1750 may include both longitudinal and hoop reinforcing fibers. The reinforcing fibers 1750 may be formed of a variety of inelastic materials, including, but not limited to, Kevlar, Vectran, Spectra, Dacron, Dyneema, Turlon (PBT), Zylon (PBO), polyimide (PIM) and other ultrahigh molecular weight polyethylenes, aramids, and the like. In some embodiments, the reinforcing fibers 1750, 1750a and/or 1750b may be aramid fibers, preferably multi-filament. In another embodiment, the reinforcing fibers 1750, 1750a and/or 1750b may be para-aramid fibers, multi-filament. In some embodiments, the material of the reinforcing fibers 1750, 1750a and/or 1750b is thermally-weldable.

Figure 18:
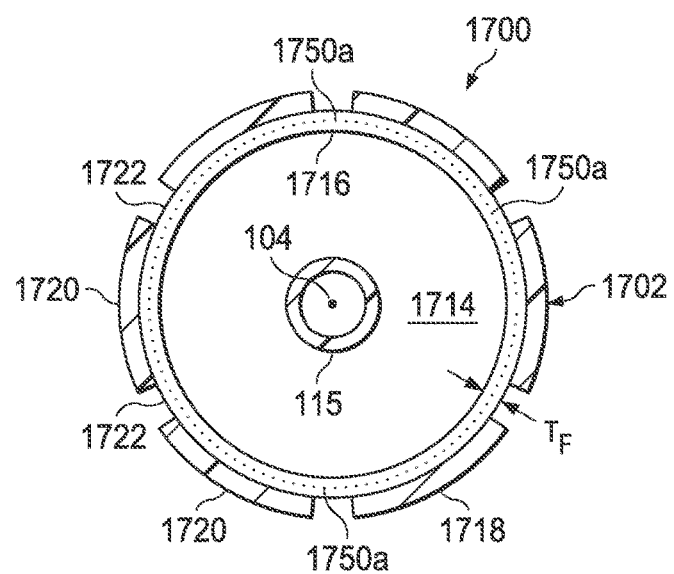
FIG. 18 is a cross-sectional view of the balloon of FIG. 17 taken along line 18-18 of FIG. 17.

Referring now also to FIG. 18, in the first embodiment illustrated in FIG. 17, the at least one elongated reinforcing fiber member 1750 comprises a plurality of longitudinally-oriented fiber members 1750a incorporated into the first layer 1716 and oriented substantially parallel to the longitudinal axis 104 of the balloon. It will be noted, in this embodiment, the second areas 1722 of reduced radial thickness of the second layer 1718 are reduced by the entire thickness of the second layer. In other embodiments (see, e.g., FIG. 20), the areas of reduced thickness 1722 may be only partially as deep as the entire thickness of the second layer 1718.

Figure 19:
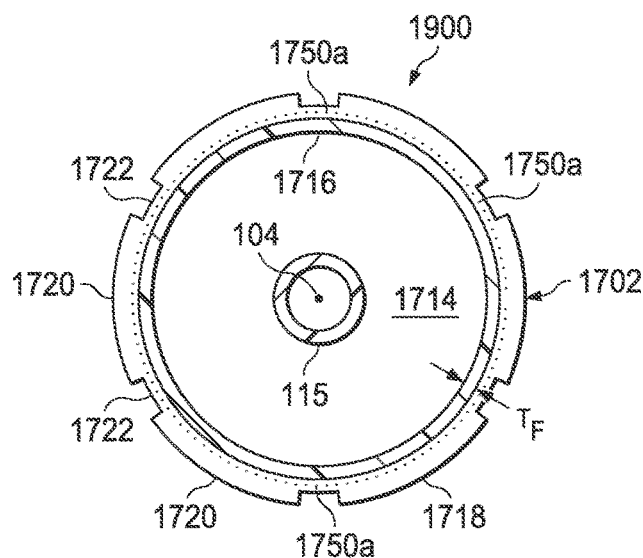
FIG. 19 is a cross-sectional view of a medical balloon in accordance with a further embodiment.

Referring now to FIG. 19, there is illustrated another embodiment of a medical balloon. The medical balloon 1900 includes at least one elongated reinforcing fiber member 1750 comprising a plurality of elongated fiber members 1750a incorporated into the second layer 1718 and oriented substantially parallel to the longitudinal axis 104 of the balloon. In other respects, balloon 1900 may be substantially similar to the balloon 1700 previously described.

Figure 20:
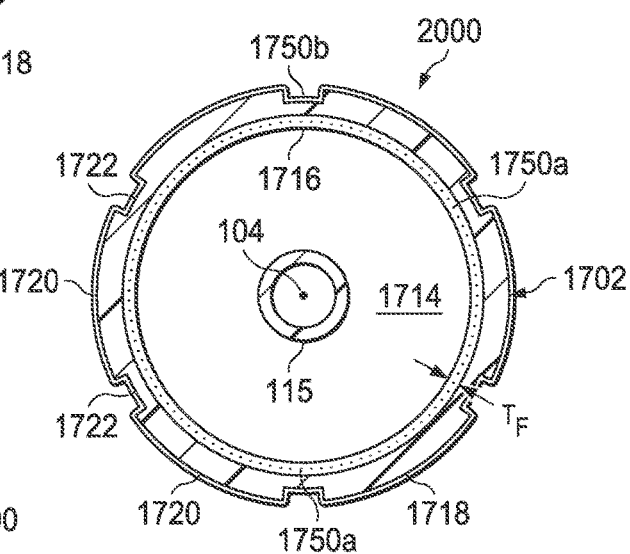
FIG. 20 is a cross-sectional view of a medical balloon in accordance with a still further embodiment.

Referring now to FIG. 20, there is illustrated another embodiment of a medical balloon. Medical balloon 2000 includes at least one elongated reinforcing fiber member 1750 comprising a plurality of elongated fiber members 1750a incorporated into the second layer 1718 and oriented substantially parallel to the longitudinal axis 104 of the balloon. The balloon 2000 further includes at least one hoop fiber 1750b oriented so as to have a spiral or helix configuration with respect to the longitudinal axis 104. In the illustrated embodiment, the hoop reinforcing fiber 1750b is disposed on the radially outer surface of second layer 1718; however, in other embodiments it may be disposed between the first layer 1716 and the second layer. In yet other embodiments (not shown), the balloon 2000 may include the hoop reinforcing fibers 1750b without including the longitudinal reinforcing fibers 1750a. In still another embodiment (not shown), the plurality of elongated fiber members 1750a incorporated into the second layer 1718 may be disposed within the first regions 1720 of greater radial thickness and not within the second regions 1722 of reduced radial thickness. In other respects, the balloon 2000 may be substantially similar to the balloon 1700 previously described.

Figure 21:
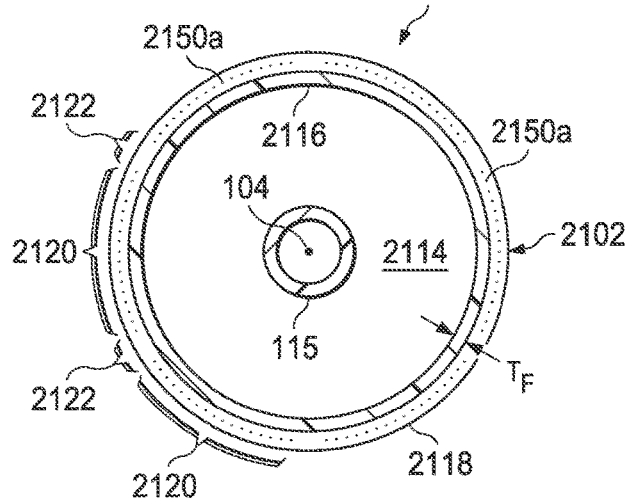
FIG. 21 is a cross-sectional view of a medical balloon in accordance with another aspect of the invention.

Referring now to FIG. 21, there is illustrated another medical balloon in accordance with an alternative embodiment. As in the medical balloons previously described herein, the medical balloon 2100 comprises a first end member disposed at a distal end of a longitudinal axis 104, second end member spaced apart from the first end member and disposed at a proximal end of the longitudinal axis, and a generally cylindrical balloon wall 2102 extending between the end members to define an inflation chamber 2114 which is adapted for inflation from a first folded configuration having a first plurality of pleats to an expanded, unpleated configuration and deflation from the expanded, unpleated configuration to a second folded configuration having a second plurality of pleats.

The balloon wall 2102 of the balloon 2100 includes a first layer 2116 formed of a polymer and having, when viewed in cross section along the longitudinal axis 104, a substantially constant radial thickness $T_F$ around the circumference. A second layer 2118 is firmly attached to the first layer 2116, the second layer having, when viewed in cross section along the longitudinal axis, a plurality of first regions 2120 of relatively greater longitudinal stiffness interleaved with a plurality of second regions 2122 of relatively reduced longitudinal stiffness. The balloon 2100 further comprises a plurality of elongated reinforcing fiber members 2150. During deflation from the expanded, unpleated configuration to the second folded configuration, the balloon wall folds along the regions of reduced longitudinal stiffness of the second layer to form the second plurality of pleats.

In the embodiment shown in FIG. 21, least some of the elongated reinforcing fibers 2150 incorporated into the second layer 2118 are longitudinally oriented fibers 2150a oriented substantially parallel to the longitudinal axis 104. The elongated reinforcing fibers 2150a incorporated into the second layer 2118 are disposed only within the first regions 2120 and not within the second regions 2122. When the fibers 2150 have greater stiffness than the material of the second layer 2118, this configuration provides the first regions 2120 (which have the fibers) with relatively greater longitudinal stiffness than the second regions 2122 (which do not have the fibers). Therefore, the balloon will tend to fold along the lines of relatively reduced longitudinal stiffness.

In other embodiments (not shown), the reinforcing fibers 2150 may further include at least one hoop fiber oriented so as to have a spiral or helix configuration with respect to the longitudinal axis 104. Such hoop fibers typically do not have a differential influence on the relative longitudinal stiffness of the first and second regions 2120 and 2122.

Although the preferred embodiment has been described in detail, it should be understood that various changes, substitutions and alterations can be made therein without departing from the spirit and scope of the invention as defined by the appended claims.

What is claimed is:

1. A medical balloon comprising:
   a first end member disposed at a distal end of a longitudinal axis;
   a second end member spaced apart from the first end member and disposed at a proximal end of the longitudinal axis; and
   a generally cylindrical balloon wall extending between the end members to define an inflation chamber which is adapted for inflation from a first folded configuration having a first plurality of pleats to an expanded, unpleated configuration and deflation from the expanded, unpleated configuration to a second folded configuration having a second plurality of pleats, the balloon wall including a first layer;
   wherein the first layer is formed of a polymer and has, when viewed in cross section along the longitudinal axis, a substantially constant radial thickness around the circumference;
   a second layer firmly attached to the first layer, the second layer having, when viewed in cross section along the longitudinal axis, a plurality of first regions of greater radial thickness interleaved with a plurality of second regions of reduced radial thickness, the second layer being made from a single layer of polymer material that fully encompasses the first layer when viewed in cross section along the longitudinal axis;
   whereby, during deflation from the expanded, unpleated configuration to the second folded configuration, the balloon wall folds along each of the second regions of reduced radial thickness of the second layer to form each pleat of the second plurality of pleats such that each pleat of the second plurality of pleats includes a fold along a second region of reduced radial thickness at a radially outer tip of the pleat and such that each adjacent pair of pleats of the second plurality of pleats includes a fold along a second region of reduced radial thickness at a position between the adjacent pair of pleats.

2. A medical balloon in accordance with claim 1, wherein the first and second end members and the first layer of the balloon wall are integrally formed from a single piece of material and the second layer is formed from a different piece of material.

3. A medical balloon in accordance with claim 2, wherein the first and second end members and the first layer of the balloon wall are formed from a single, seamless tube of material that has been blow-molded.

4. A medical balloon in accordance with claim 2, wherein the first and second end members and the first layer of the balloon wall are formed from a single, seamless tube of polyethylene terephthalate (PET) material.

5. A medical balloon in accordance with claim 2, wherein the first and second end members and the first layer of the balloon wall are formed from a single, seamless tube of nylon (polyamide) material.

6. A medical balloon in accordance with claim 2, wherein the second layer overlies, in the longitudinal direction, less than substantially the entire length of the balloon wall and does not overlie any of the first or second end members.

7. A medical balloon in accordance with claim 2, wherein the second layer overlies, in the longitudinal direction, substantially the entire length of the balloon wall but does not overlie any of the first or second end members.

8. A medical balloon in accordance with claim 2, wherein the second layer overlies, in the longitudinal direction, substantially the entire length of the balloon wall and at least a portion of the first and/or second end members.

9. A medical balloon in accordance with claim 8, wherein the plurality of first regions of greater radial thickness interleaved with the plurality of second regions of reduced radial thickness extend, in the longitudinal direction, from at least a portion of the balloon wall onto at least a portion of one of the first and/or second end members.

10. A medical balloon in accordance with claim 2, wherein at least some of the second regions of reduced radial thickness include intermittent areas of different radial thickness along their longitudinal length.

11. A medical balloon in accordance with claim 2, wherein the second regions of reduced radial thickness are oriented substantially parallel to the longitudinal axis of the balloon.

12. A medical balloon in accordance with claim 2, wherein the second regions of reduced radial thickness are oriented substantially in the shape of a helix or spiral around the longitudinal axis of the balloon.

13. A medical balloon comprising:
a first end member disposed at a distal end of a longitudinal axis;
a second end member spaced apart from the first end member and disposed at a proximal end of the longitudinal axis; and
a generally cylindrical balloon wall extending between the end members to define an inflation chamber which is adapted for inflation from a first folded configuration having a first plurality of pleats to an expanded, unpleated configuration and deflation from the expanded, unpleated configuration to a second folded configuration having a second plurality of pleats, the balloon wall including a first layer;
wherein the first layer is formed of a polymer and has, when viewed in cross section along the longitudinal axis, a substantially constant radial thickness around the circumference;
a second layer firmly attached to the first layer, the second layer having, when viewed in cross section along the longitudinal axis, a plurality of first regions of greater radial thickness interleaved with a plurality of second regions of reduced radial thickness, the second layer being made from a single layer of polymer material that fully encompasses the first layer when viewed in cross section along the longitudinal axis; and
at least one elongated reinforcing fiber member;
whereby, during deflation from the expanded, unpleated configuration to the second folded configuration, the balloon wall folds along each of the second regions of reduced radial thickness of the second layer to form each pleat of the second plurality of pleats such that each pleat of the second plurality of pleats includes a fold along a second region of reduced radial thickness at a radially outer tip of the pleat and such that each adjacent pair of pleats of the second plurality of pleats includes a fold along a second region of reduced radial thickness at a position between the adjacent pair of pleats.

14. A medical balloon in accordance with claim 13, wherein the at least one elongated reinforcing fiber member comprises a plurality of elongated fiber members incorporated into the first layer and oriented substantially parallel to the longitudinal axis of the balloon.

15. A medical balloon in accordance with claim 13, wherein the at least one elongated reinforcing fiber member comprises a plurality of elongated fiber members incorporated into the second layer and oriented substantially parallel to the longitudinal axis of the balloon.

16. A medical balloon in accordance with claim 15, wherein the plurality of elongated fiber members incorporated into the second layer are disposed within the first regions of greater radial thickness and not within the second regions of reduced radial thickness.

17. A medical balloon in accordance with claim 13, wherein the at least one elongated reinforcing fiber member is oriented substantially in the shape of a helix or spiral around the longitudinal axis of the balloon.

18. A medical balloon comprising:
a first end member disposed at a distal end of a longitudinal axis;
a second end member spaced apart from the first end member and disposed at a proximal end of the longitudinal axis; and
a generally cylindrical balloon wall extending between the end members to define an inflation chamber which is adapted for inflation from a first folded configuration having a first plurality of pleats to an expanded, unpleated configuration and deflation from the expanded, unpleated configuration to a second folded configuration having a second plurality of pleats, the balloon wall including a first layer;
wherein the first layer is formed of a polymer and has, when viewed in cross section along the longitudinal axis, a substantially constant radial thickness around the circumference;
a second layer firmly attached to the first layer, the second layer having, when viewed in cross section along the longitudinal axis, a plurality of first regions of relatively greater longitudinal stiffness interleaved with a plurality of second regions of relatively reduced longitudinal stiffness, the second layer being made from a single layer of polymer material that fully encompasses the first layer when viewed in cross section along the longitudinal axis; and
a plurality of elongated reinforcing fiber members;
whereby, during deflation from the expanded, unpleated configuration to the second folded configuration, the balloon wall folds along each of the second regions of reduced longitudinal stiffness of the second layer to form each pleat of the second plurality of pleats such that each pleat of the second plurality of pleats includes a fold along a second region of reduced longitudinal stiffness at a radially outer tip of the pleat and such that each adjacent pair of pleats of the second plurality of pleats includes a fold along a second region of reduced longitudinal stiffness at a position between the adjacent pair of pleats.

* * * * *